United States Patent
Yanagawa et al.

(10) Patent No.: US 7,622,618 B2
(45) Date of Patent: Nov. 24, 2009

(54) METHOD FOR HYDRATING OLEFINS

(75) Inventors: Shinichiro Yanagawa, Yokohama (JP); Michikazu Hara, Yokohama (JP)

(73) Assignees: Nippon Oil Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 12/085,853

(22) PCT Filed: Nov. 30, 2006

(86) PCT No.: PCT/JP2006/324408

§ 371 (c)(1), (2), (4) Date: May 30, 2008

(87) PCT Pub. No.: WO2007/064041

PCT Pub. Date: Jun. 7, 2007

(65) Prior Publication Data

US 2009/0137850 A1   May 28, 2009

(30) Foreign Application Priority Data

Dec. 1, 2005   (JP) .............................. 2005-348038

(51) Int. Cl.
*C07C 29/04*   (2006.01)
(52) U.S. Cl. ...................................... 568/895; 568/899
(58) Field of Classification Search ................ 568/895, 568/899
See application file for complete search history.

(56) References Cited

U.S. PATENT DOCUMENTS

2006/0276668 A1   12/2006   Domen et al.

FOREIGN PATENT DOCUMENTS

JP          2004-238311        8/2004
WO    WO 2005/029508 A1    3/2005

OTHER PUBLICATIONS

Shokubai (Catalysts & Catalysis), vol. 18, No. 6, pp. 180-184, 1976.
Sekiyu Gakkaishi (Journal of the Japan Petroleum Institute), vol. 34, No. 3, pp. 201-209, 1991.
Atushi Takagaki, Junko Nomura, Michikazu Hara, Shigenobu Hayashi and Kazunari Domen: "Carbon-based strong solid acids: synthesis conditions and catalysis", 85th Annual Meeting (Spring) of the Chemical Society of Japan (2005), 2B5-43.
ANGEW. Chem. Int. Ed., 43, 2955-2958 (2004).
Nature, 438, 10, p. 178, Nov. 2005.

*Primary Examiner*—Sikarl A Witherspoon
(74) *Attorney, Agent, or Firm*—Weingarten, Schurgin, Gagnebin & Lebovici LLP

(57) ABSTRACT

A novel olefin hydration method is provided for efficiently producing alcohols by hydration of olefins containing 2 to 5 carbon atoms in the presence of a catalyst. Thus, alcohols are produced by hydrating olefins containing 2 to 5 carbon atoms at reaction temperature of 100 to 250° C. in the presence of a solid acid catalyst consisting of carbonaceous materials containing sulfonic acid groups obtained from an organic matter by carbonization and sulfonation. In carrying out this method, the organic matter is preferably an aromatic hydrocarbon or a saccharide, the olefin is preferably propylene or a butenes, and the hydration reaction temperature is not lower than 120° C., more preferably not lower than 150° C.

8 Claims, No Drawings

METHOD FOR HYDRATING OLEFINS

This application is a §371 national phase filing of PCT/JP2006/324408 filed Nov. 30, 2006, and claims priority to Japanese application No. 2005-348038 filed Dec. 1, 2005.

TECHNICAL FIELD

The present invention relates to a method of carrying out the hydration reaction of olefins in the presence of a carbon-based solid acid catalyst.

BACKGROUND ART

The olefin hydration reaction is an important reaction for the production of alcohols, and is utilized industrially. Isopropyl alcohol and 2-butanol are produced by various methods utilizing the hydration of propylene or n-butene (Non-Patent Document 1 and Non-Patent Document 2). The method currently employed in the plants in the world is the method comprising reacting propylene or n-butene with sulfuric acid and hydrolyzing the resulting sulfate ester (indirect hydration). This method has problems, however; for example, byproduct formation is significant, sulfuric acid is required in large amounts, and also has such problems as apparatus corrosion by sulfuric acid, recycling of sulfuric acid and waste liquid treatment. Also available are methods using various catalysts in direct hydration. For example, there are methods using an ion exchange resin as a catalyst and methods using, as a catalyst, a solid acid comprising phosphoric acid or a like mineral acid supported on a carrier. However, the ion exchange group (sulfonic acid group) may be eliminated by hydrolysis or the acid supported on carrier may be detached from the carrier during reaction to cause a decrease in activity and/or apparatus corrosion. It becomes necessary to take measures against such cases. And more, in the case of an ion exchange resin catalyst, there are also such problems, for example, that the catalyst is expensive and that the reaction temperature is restricted due to the poor heat resistance property of the resin. Also known are the methods which use a homogeneous molybdenum- or tungsten-based polyanion solution (aqueous heteropolyacid solution) as a catalyst; but they require high-temperature and high-pressure reaction conditions, however. In any case, in olefin hydration reaction method, the use of an acid catalyst is essential and each method has problems due to catalyst properties.

On the other hand, various acid catalysts are used in various reactions in industrial processes. From point of view of catalyst performance, energy saving and cost, catalysts excellent in these points are required. Solid acid catalysts, in particular, are promising since they will make it possible to simplify processes. Thus, various such catalysts have been developed. Among them, recently developed carbon-based solid acids obtained by carbonization and sulfonation of organic matters have attracted attention and applications thereof have been attempted (Non-Patent Document 3, Non-Patent Document 5, Patent Document 1 and Patent Document 2). As regards the olefin hydration reaction, an example is known in which 2,3-dimethyl-2-butene was subjected to the reaction at a low temperature (70° C.) but nothing is known about the hydration reaction of lower olefins differing in reactivity therefrom (Non-Patent Document 4).

Non-Patent Document 1: Shokubai (Catalysts & Catalysis), Vol. 18, No. 6, pp. 180-184, 1976

Non-Patent Document 2: Sekiyu Gakkaishi (Journal of the Japan Petroleum Institute), Vol. 34, No. 3, pp. 201-209, 1991

Non-Patent Document 3: Atushi Takagaki, Junko Nomura, Michikazu Hara, Shigenobu Hayashi and Kazunari Domen: "Carbon-based strong solid acids: synthesis conditions and catalysis", 85th Annual Meeting (Spring) of the Chemical Society of Japan (2005), 2B5-43

Non-Patent Document 4: Angew. Chem. Int. Ed., 43, 2955-2958 (2004)

Non-Patent Document 5: Nature, 438, 10, p. 178, November, 2005

Patent Document 1: Japanese Patent (Laid-Open) Publication No. 2004-238311

Patent Document 2: International Patent Publication No. WO2005/029508

DISCLOSURE OF INVENTION

It is an object of the invention to provide a method of hydrating olefins utilizing a novel catalytic activity for efficiently producing alcohols by the hydration reaction of olefins.

In a first aspect, the invention relates to a method of hydrating olefins which is characterized in that the hydration reaction of an olefin containing 2 to 5 carbon atoms to give the corresponding alcohol is carried out, at 100° C. to 250° C., in the presence of a solid acid catalyst consisting of carbonaceous materials containing sulfonic acid groups obtained by carbonization and sulfonation of an organic matter.

In a second aspect, the invention relates to a method of hydrating olefins which is carried out in accordance with the first aspect and is characterized in that the organic matter is an aromatic hydrocarbon or a saccharide.

In a third aspect, the invention relates to a method of hydrating olefins which is carried out in accordance with the first or second aspect and is characterized in that the olefin is propylene or a butanes.

In a fourth aspect, the invention relates to a method of hydrating olefins which is carried out in accordance with the first, second or third aspect and is characterized in that the hydration reaction temperature is not lower than 120° C.

In a fifth aspect, the invention relates to a method of hydrating olefins which is carried out in accordance with the first, second or third aspect and is characterized in that the hydration reaction temperature is not lower than 150° C.

EFFECTS OF THE INVENTION

The method according to the invention can produce alcohols at low cost and with high efficiency since the olefin hydration reaction activity is high, no neutralization and purification processes are required after reaction, the catalyst can be easily separated and reused and no apparatus corrosion problem arises.

BEST MODES FOR CARRYING OUT THE INVENTION

In the following, the invention is described in further detail.

The solid acid catalyst consisting of carbonaceous materials containing sulfonic acid groups to be used in the practice of the invention is obtained by carbonization and sulfonation of an organic matter, and those disclosed in the above-cited documents Non-Patent Document 3, Non-Patent Document 5 and Patent Document 1 can be used.

The organic matter to serve as a raw material for the above-mentioned solid acid catalyst is not particularly restricted if provided that it can be carbonized and sulfonated. Preferred are, however, aromatic hydrocarbons and saccharides.

Among the aromatic hydrocarbons, naphthalene, anthracene, perylene, coronene and like polycyclic aromatic hydrocarbons, in particular those comprising 5 or more fused aromatic rings, are preferred. Materials containing such aromatic hydrocarbons, for example pitch and tar, may also be used. As the saccharides, there may be mentioned monosaccharides such as glucose and polysaccharides such as maltose, sucrose and cellulose. These organic matters may also be used in admixture.

The carbonization of the organic matter is carried out by heat treatment in an inert gas atmosphere such as a nitrogen atmosphere, whereby an amorphous black solid (carbonization product) is obtained. The sulfonation is carried out by heat treatment in concentrated sulfuric acid or oleum (fuming sulfuric acid), whereby sulfonic groups are added to the skeleton of the carbonization product mentioned above. The sulfonation may be carried out after carbonization or simultaneously with carbonization, and the carbonization and sulfonation temperature may be properly selected depending on the organic matter species employed. The sulfonated carbonization product is washed with hot water to remove the excess sulfuric acid and is further dried to give a solid acid catalyst consisting of carbonaceous materials containing sulfonic acid groups suited for use in the practice of the invention.

In the case of a polycyclic aromatic hydrocarbon being used as the organic matter, the carbonization and sulfonation are preferably carried out simultaneously by treatment in concentrated sulfuric acid or oleum for 2 to 50 hours, preferably 5 to 20 hours at 100 to 450° C., preferably 200 to 350° C.

In the case of a saccharide being used as the organic matter, the saccharide is preferably carbonized by calcining at 250 to 600° C., preferably 350 to 500° C., for 1 to 30 hours, followed by sulfonation by heat treatment in concentrated sulfuric acid or oleum at 40 to 450° C., preferably 100 to 350° C. for 0.5 to 30 hours.

The acid group content (determined by back titration) of the carbon-based solid acid to be used in the practice of the invention is not lower than 0.5 mmol/g, preferably 1 to 8 mmol/g.

The solid acid catalyst consisting of carbonaceous materials containing sulfonic acid groups obtained as mentioned above, can be prepared using simple and easy method using inexpensive raw materials, hence can be produced at low cost. Further, since the sulfonic acid groups are immobilized in the solid catalyst, the catalyst, when used in the hydration reaction, causes no such apparatus corrosion problem as encountered when liquid sulfuric acid is used.

The olefin containing 2 to 5 carbon atoms, which is to be used in the practice of the invention, is not particularly restricted and may be straight-chain, branched or cyclic. Preferred are, however, propylene and butenes such as 1-butene, 2-butene and isobutene. While the water to be used for hydration is not particularly restricted, ion-exchange water and distilled water (including steam condensate water) are preferably used. The mole ratio of water to the olefin is not particularly restricted but generally is 0.1 to 10, preferably 0.3 to 7, more preferably 1 to 5. An excessively small amount of water may lead to such a side reaction as olefin dimerization, while an excessively large amount of water unfavorably causes decreases in productivity.

In the olefin hydration reaction, it is necessary that the reaction temperature be 100° C. to 250° C. and, for attaining higher levels of activity, the reaction temperature is preferably not lower than 120° C., more preferably not lower than 150° C. The temperature should not exceed 250° C. since the catalyst may possibly be decomposed at higher temperatures.

For proceeding the reaction, the reaction pressure is not lower than 1 MPa, preferably not lower than 3 MPa, more preferably not lower than 5 MPa. The pressure is preferably not higher than 20 MPa since higher pressures lead to increases in equipment cost. The reaction pressure may be selected appropriately depending on the reaction mode. As for the reaction mode, any of the gaseous phase, liquid phase and gas-liquid mixed phase modes may be employed.

In carrying out the hydration reaction, it is also possible to use a solvent. The solvent is preferably an amphiphilic one so that the reaction solution may not separate into an aqueous phase and an oil phase. Thus, for example, ethers, glycol ethers, alcohols and ketones, can be used.

The method according to the invention is direct hydration (single stage reaction) and, therefore, the process is simpler as compared with the indirect hydration method (two-stage reaction, namely sulfuric acid esterification and hydrolysis) using sulfuric acid catalyst. Further, while the indirect hydration method requires the step of neutralization/purification process for removing sulfuric acid and the step of concentration for the reuse of sulfuric acid, and therefore is complicated in procedure, the method according to the invention, which uses a solid catalyst, makes it possible to separate the catalyst with ease by filtration or centrifugation, for instance, for reusing of the same and, furthermore, makes it unnecessary to carry out such neutralization/purification process as required by the indirect hydration method, since the reaction solution after removal of the catalyst no longer contains the acid catalyst component. After catalyst removal, the product can be appropriately purified by distillation, for instance.

EXAMPLES

The following examples illustrate the present invention more specifically. They are, however, by no means limitative of the scope of the invention.

Catalyst Production Example 1

Glucose (20 g) was heat-treated in a nitrogen atmosphere at 400° C. for 15 hours to give a carbonization product. To this carbonization product was added 100 mL of oleum ($SO_3$: 25%), and the mixture was heat-treated in a nitrogen atmosphere at 150° C. for 15 hours for sulfonation. The excess sulfuric acid was removed by distillation under reduced pressure at 250° C. for 5 hours to give a solid product. This solid product was washed repeatedly with hot water; after five repetitions of washing, sulfuric acid was no longer detected in the washing water. Finally, the solid was dried to give a black powder (carbon-based solid acid catalyst A). The acid group content of the catalyst as determined by back titration was 3.1 mmol/g.

The carbon-based solid acid catalyst A was subjected to X ray analysis. The X-ray analysis was carried out using a MacScience X-ray diffractometer (MXP18VAHF). As a result, the analytical pattern of the solid acid showed no peak detectable for structure identification, revealing that it was an amorphous substance.

Catalyst Production Example 2

A carbon-based solid acid catalyst (catalyst B) was obtained as a black powder in the same manner as in Example 1 except that concentrated sulfuric acid (96%) was used in lieu of oleum. The acid group content of the catalyst as determined by back titration was 3.3 mmol/g. The results of X-ray analysis revealed that it was amorphous.

Catalyst Production Example 3

Naphthalene (10 g) was added to 100 mL of concentrated sulfuric acid (96%), and the mixture was heat-treated in a nitrogen atmosphere at 250° C. for 15 hours. Then, the excess concentrated sulfuric acid was removed by reduced pressure distillation at 250° C. for 5 hours to give a carbonized solid matter. Further, this solid was washed repeatedly with hot water; after five repetitions of washing, sulfuric acid was no longer detected in the washing water. Finally, the solid was dried to give a carbon-based solid acid catalyst (catalyst C) as a black powder. The acid group content of the catalyst as determined by back titration was 2.7 mmol/g. The results of X-ray analysis revealed that it was amorphous.

Hydration Reaction Examples 1 to 7 and Comparative Examples 1 and 2

A 50 cc autoclave equipped with a stirrer was charged with 9 g of water and 15 g of dioxane (solvent) and, after addition of a specified amount of the carbon-based solid acid catalyst A, B or C obtained in above-mentioned Examples 1 to 3, the autoclave was hermetically closed, followed by injection of specified amount of propylene or 1-butene. Then, the temperature was raised to a specified level with stirring at 700 rpm and, if necessary, after pressure adjustment with nitrogen, the hydration reaction was allowed to proceed for 2 hours while the temperature was maintained at the specified level. After completion of the reaction, the reaction solution was cooled and then subjected to quantitative analysis by TCD-GC (thermal conductivity detector gas chromatography). The reaction conditions and reaction results (Examples 1 to 7 and Comparative Examples 1 and 2) are shown in Table 1.

Comparative Examples 3 and 4

The hydration reaction was carried out in the same manner as in the above examples except that the carbon-based solid acid catalyst B obtained in Catalyst Production Example 2 was used and 1-hexene was used as the reactant. The reaction conditions and reaction results are shown in Table 1.

Comparative Examples 5 and 6

The hydration reaction was carried out in the same manner as in the examples mentioned above except that the anion exchange resin Amberlyst (acid group content 4.2 mmol/g) (Comparative Example 5) or sulfuric acid (acid group content 20.4 mmol/g) (Comparative Example 6) was used in lieu of the carbon-based solid acid catalyst. In Comparative Example 6 in which sulfuric acid was used, the experiment was carried out not in the manner of indirect hydration but in the manner of direct hydration. The reaction conditions and reaction results are shown in Table 1.

The results of Examples 1, 4 and 6 and Comparative Example 6 indicate that the solid acid catalysts consisting of carbonaceous materials containing sulfonic acid groups are at least comparable in activity to the sulfuric acid catalyst high in acid group content. Further, the results of Examples 2, 5 and 7 and Comparative Example 5 indicate that when used at a higher temperature (180° C.) as compared with the heat resistance upper limit temperature (120° C.) of Amberlyst, the solid acid catalysts consisting of carbonaceous materials containing sulfonic acid groups show higher activity as compared with Amberlyst higher in acid group content. Furthermore, the results of Comparative Examples 1 and 2 indicate that the reaction will not proceed at relatively low temperatures and, further, the results of Comparative Examples 3 and 4 indicate that the reaction will not proceed with 1-hexene.

TABLE 1

Reaction Conditions and Reaction Results

| | | Catalyst | Olefin | Water (mol) | Temperature (° C.) | Pressure (MPa) | Alcohol formed |
|---|---|---|---|---|---|---|---|
| Example | 1 | Carbon-based solid acid catalyst A | Propylene 0.21 mol | 0.5 | 120 | 5 | Isopropyl alcohol 0.12 mmol |
| | 2 | 0.20 g (Acid group content: 0.62 mmol) | Propylene 0.21 mol | 0.5 | 180 | 7.7 | Isopropyl alcohol 4.5 mmol |
| | 3 | | 1-Butene 0.25 mol | 0.5 | 180 | 6.1 | 2-Butanol 10 mmol |
| | 4 | Carbon-based solid acid catalyst B | Propylene 0.24 mol | 0.5 | 120 | 5 | Isopropyl alcohol 0.12 mmol |
| | 5 | 0.20 g (Acid group content: 0.66 mmol) | Propylene 0.33 mol | 0.5 | 180 | 7.4 | Isopropyl alcohol 24 mmol |
| | 6 | Carbon-based solid acid catalyst C | Propylene 0.24 mol | 0.5 | 120 | 5 | Isopropyl alcohol 0.24 mmol |
| | 7 | 0.20 g (Acid group content: 0.54 mmol) | Propylene 0.24 mol | 0.5 | 180 | 7.2 | Isopropyl alcohol 4.0 mmol |
| Comparative Example | 1 | Carbon-based solid acid catalyst B 0.20 g | Propylene 0.24 mol | 0.5 | 70 | 2.7 | No alcohol formed |
| | 2 | | 1-Butene 0.24 mol | 0.5 | 70 | 2.5 | No alcohol formed |
| | 3 | | 1-Hexene 0.24 mol | 0.5 | 70 | 2.5 | No alcohol formed |

TABLE 1-continued

Reaction Conditions and Reaction Results

| | Catalyst | Olefin | Water (mol) | Temperature (° C.) | Pressure (MPa) | Alcohol formed |
|---|---|---|---|---|---|---|
| 4 | | 1-Hexene 0.24 mol | 0.5 | 120 | 3.0 | No alcohol formed |
| 5 | Amberlyst 15 dry 0.20 g (Acid group content: 0.84 mmol) | Propylene 0.20 mol | 0.5 | 120 | 5 | Isopropyl alcohol 2.2 mmol |
| 6 | $H_2SO_4$ 0.045 g (Acid group content: 0.92 mmol) | Propylene 0.22 mol | 0.5 | 120 | 5 | Isopropyl alcohol 0.12 mmol |

INDUSTRIAL APPLICABILITY

According to the method of the invention, high levels of olefin hydration reaction activity can be attained, no neutralization/purification step is required after reaction, the catalyst can be readily separated and reused, no apparatus corrosion problem will arise, and alcohols can be produced at low cost and with high efficiency. Therefore, the method according to the invention in the present application can be industrially utilized as a method of producing alcohols from olefins at low cost and with ease.

The invention claimed is:

1. A method of hydrating olefins comprising carrying out an hydration reaction of an olefin containing 2 to 4 carbon atoms to give alcohol at 120° C. to 250° C. in the presence of a solid acid catalyst consisting of carbonaceous materials containing sulfonic acid groups obtained by carbonization and sulfonation of an organic matter.

2. A method of hydrating olefins according to claim 1, wherein the organic matter is an aromatic hydrocarbon or a saccharide.

3. A method of hydrating olefins according to claim 1, wherein the olefin is a propylene or a butene.

4. A method of hydrating olefins according to claim 1, wherein the hydration reaction temperature is 150° C. to 250° C.

5. A method of hydrating olefins according to claim 2, wherein the olefin is a propylene or a butene.

6. A method of hydrating olefins according to claim 2, wherein the hydration reaction temperature is 150° C. to 250° C.

7. A method of hydrating olefins according to claim 3, wherein the hydration reaction temperature is 150° C. to 250° C.

8. A method of hydrating olefins according to claim 5, wherein the hydration reaction temperature is 150° C. to 250° C.

* * * * *

UNITED STATES PATENT AND TRADEMARK OFFICE
CERTIFICATE OF CORRECTION

PATENT NO. : 7,622,618 B2
APPLICATION NO. : 12/085853
DATED : November 24, 2009
INVENTOR(S) : Shinichiro Yanagawa et al.

It is certified that error appears in the above-identified patent and that said Letters Patent is hereby corrected as shown below:

Title page, (75) Inventors, "Shinichiro Yanagawa, Yokohama" should read --Shinichiro Yanagawa, Yokohama-Shi--;

Title page, (75) Inventors, "Michikazu Hara, Yokohama" should read --Michikazu Hara, Yokohama-Shi--;

Title page, (54) Title, "METHOD FOR HYDRATING OLEFINS" should read --METHOD OF HYDRATING OLEFINS--; and Column 1, line 1, "METHOD FOR HYDRATING OLEFINS" should read --METHOD OF HYDRATING OLEFINS--.

Signed and Sealed this

Twenty-fourth Day of August, 2010

David J. Kappos
*Director of the United States Patent and Trademark Office*